United States Patent
Yano et al.

(10) Patent No.: US 6,812,013 B2
(45) Date of Patent: Nov. 2, 2004

(54) POLYHYDROXYALKANOATE SYNTHASE AND GENE ENCODING THE SAME

(75) Inventors: Tetsuya Yano, Kanagawa (JP); Takeshi Imamura, Kanagawa (JP); Sakae Suda, Ibaraki (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/245,765

(22) Filed: Sep. 18, 2002

(65) Prior Publication Data

US 2003/0124692 A1 Jul. 3, 2003

Related U.S. Application Data

(63) Continuation-in-part of application No. 09/820,721, filed on Mar. 30, 2001, now abandoned.

(30) Foreign Application Priority Data

Mar. 30, 2000 (JP) .................................. 2000-095005

(51) Int. Cl.[7] .......................... C12N 9/02; C12N 15/00; C12P 21/04; C12Q 1/68; C07H 21/04

(52) U.S. Cl. .......................... 435/189; 435/6; 435/71.1; 435/252.3; 435/320.1; 435/440; 536/23.2

(58) Field of Search ............................. 435/189, 71.1, 435/6, 252.3, 320.1, 440; 536/23.2

(56) References Cited

U.S. PATENT DOCUMENTS

| | | | |
|---|---|---|---|
| 4,393,167 A | 7/1983 | Holmes et al. | 525/64 |
| 4,477,654 A | 10/1984 | Holmes et al. | 528/361 |
| 5,135,859 A | 8/1992 | Witholt et al. | 435/135 |
| 5,200,332 A | 4/1993 | Yamane et al. | 435/135 |
| 5,292,860 A | 3/1994 | Shiotani et al. | 528/361 |
| 5,849,894 A | 12/1998 | Clemente et al. | 536/23.2 |
| 5,968,805 A | 10/1999 | Doi et al. | 435/252.3 |
| 6,485,951 B2 | 11/2002 | Yano et al. | 435/190 |
| 2001/0046692 A1 | 11/2001 | Yano et al. | 435/135 |
| 2001/0053544 A1 | 12/2001 | Yano et al. | 435/196 |

(List continued on next page.)

FOREIGN PATENT DOCUMENTS

| | | |
|---|---|---|
| EP | 0 897 005 | 12/1999 |
| EP | 1 120 461 | 8/2001 |
| JP | 5-7492 | 3/1993 |
| JP | 5-93049 | 4/1993 |
| JP | 6-15604 | 1/1994 |
| JP | 7-14352 | 1/1995 |
| JP | 7-265065 | 10/1995 |
| JP | 2642937 | 5/1997 |
| JP | 9-191893 | 7/1997 |
| WO | WO 91/00917 | 1/1991 |
| WO | WO 01/11014 | 2/2001 |

OTHER PUBLICATIONS

K. Fritzsche et al., "An Unusual Bacterial Polyester With a Phenyl Pendant Group," 191 *Makromol. Chem.* 1957–1965 (1990).
J. Marmur, "A Procedure for the Isolation of Deoxyribonucleic Acid From Micro–Organisms," 3 *J. Mol. Biol.* 208–218 (1961).
*Methods in Enzymology*, vol. 68, p. 253 (1979).
O. Peoples et al., "Poly–β–hydroxybutyrate Biosynthesis in *Alcaligenes eutrophus* H16," 264(26) *J. Biol. Chem.* 15293 (1989).
G. W. Huisman et al., "Metabolism of Poly(3–hydroxyalkanoates) (PHAs) by *Pseudomonas oleovorans*," 266*J. Biol. Chem.* 2191 (1991).
U. Pleper et al., "Identification, Cloning and Sequence Analysis of the Poly(3–hydroxialkan ic acid) Synthase Gene of the Gram–Positive Bacterium *Rhodococcus ruber*," 96 *FEMS Microbiol I. Lett.* 73 (1992).
A. Timm et al., "Cloning and Molecular Analysis of the Poly(3–hydroxyalkanoic acid) Gene Locus of *Pseudomonas aeruginosa* PAO1," 209 *Eur. J. Biochem.* 15 (1992).
H. Matsusaki et al., "Cloning and Molecular Analysis of the Poly)3–hydroxybutyrate) and Poly(3–hydroxybutyrate)–co–3–hydroxyalkanoate) Biosynthesis Genes in *Pseudomonas* sp. Strain 61–3," 180(24) *J. Bacteriol.* 6459 (1998).
H. Matsusake et al., "PHA Synthase 1" Retrieved from EBI, Database Accession No. Q9Z3Y1, May 1, 1999 (XP–002176385), Abstract.
H. Matsusake et al., "PHA Synthase 2" Retrieved from EBI, Database Accession No. Q9Z3X9, May 1, 1999 (XP–002176384), Abstract.
H. Matsusake et al., "*Pseudomonas* sp. 61–3 Genes for PHA Synthase 1, PHA Depolymerase, PHA Synthase 2 and PhaD, Complete CDs" Retrieved from EBI, Database Accession No. AB014758, Dec. 12, 1998 (XP–002176386), Abstract.
Belén Garcia et al., "Novel Biodegradable Aromatic Plastics from a Bacterial Source," 274(41) *J. Biol. Chem.* 29228–28241 (1999).
D.M. Becker et al., "High–Efficiency Transformation of Yeast by Electroporation," 194 *M thods Enzymol.* 182–187 (1990).
H. Ito et al., "Transformation of Intact Yeast Cells Treated with Alkali Cations," 153(1) *J. Bacteriol.* 163–168 (1983).
A. Hinnen et al., "Transformation of Yeast," 75(4) *Proc. Natl. Acad. Sci.* 1929–1933 (1978).

*Primary Examiner*—P. Achutamurthy
*Assistant Examiner*—Yong D. Pak
(74) *Attorney, Agent, or Firm*—Fitzpatrick, Cella, Harper & Scinto

(57) ABSTRACT

The present invention provides a PHA (polyhydroxyalkanoate) synthase useful in a process for preparing a PHA, a gene encoding the enzyme, a recombinant vector comprising the gene, a transformant transformed by the vector, a process for producing a PHA synthase utilizing the transformant and a process for preparing a PHA utilizing the transformant. A transformant obtained by introducing a PHA synthase gene from *Pseudomonas putida* P91 strain into a host microorganism is cultured to produce a PHA synthase or PHA.

4 Claims, No Drawings

U.S. PATENT DOCUMENTS

| | | | |
|---|---|---|---|
| 2001/0055795 A1 | 12/2001 | Yano et al. | 435/135 |
| 2002/0098565 A1 | 7/2002 | Yano et al. | 435/196 |
| 2003/0049806 A1 | 3/2003 | Yano et al. | 435/135 |
| 2003/0077746 A1 | 4/2003 | Yano et al. | 435/69.1 |
| 2003/0082777 A1 | 5/2003 | Yano et al. | 435/196 |
| 2003/0087413 A1 | 5/2003 | Yano et al. | 435/196 |
| 2003/0092141 A1 | 5/2003 | Yano et al. | 435/135 |

SEQUENCE LISTING

```
<160> NUMBER OF SEQ ID NOS: 10
<210> SEQ ID NO 1
<211> LENGTH: 559
<212> TYPE: PRT
<213> ORGANISM: Pseudomonas putida P91
<220> FEATURE:
<223> OTHER INFORMATION: Polyhydroxyalkanoate synthase

<400> SEQUENCE: 1

Met Ser Asn Lys Asn Asn Asp Asp Leu Gln Arg Gln Ala Ser Glu Asn
1               5                   10                  15

Thr Leu Gly Leu Ser Pro Ile Ile Gly Leu Arg Arg Lys Asp Leu Leu
            20                  25                  30

Ser Ser Ala Arg Met Val Leu Arg Gln Ala Ile Lys Gln Pro Leu His
        35                  40                  45

Ser Ala Lys His Val Ala His Phe Gly Leu Gln Leu Lys Asp Val Ile
    50                  55                  60

Phe Gly Lys Ser Gly Leu Gln Pro Glu Gly Asp Asp Arg Arg Phe Ser
65                  70                  75                  80

Asp Pro Ala Trp Ser Gln Asn Pro Leu Tyr Arg Arg Tyr Leu Gln Thr
                85                  90                  95

Tyr Leu Ala Trp Arg Lys Glu Leu His Asp Trp Ile Gly Asn Ser Asn
            100                 105                 110

Leu Ser Glu Gln Asp Ile Ser Arg Ala His Phe Val Ile Asn Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Met Val His Asn Gly Gly Met Pro Ser Gln Val
                165                 170                 175

Asn Met Asp Ala Phe Glu Val Gly Lys Asn Leu Ala Thr Thr Glu Gly
            180                 185                 190

Ala Val Val Phe Arg Asn Asp Val Leu Glu Leu Ile Gln Tyr Arg Pro
        195                 200                 205

Ile Thr Glu Gln Val His Glu Lys Pro Leu Leu Val Val Pro Pro Gln
    210                 215                 220
```

-continued

```
Ile Asn Lys Phe Tyr Val Phe Asp Leu Ser Pro Glu Lys Ser Leu Ala
225                 230                 235                 240

Arg Phe Cys Leu Arg Ser Thr Val Gln Thr Phe Ile Val Ser Trp Arg
            245                 250                 255

Asn Pro Asn Lys Ser Gln Arg Glu Trp Gly Leu Ser Tyr Ile Asp
        260                 265                 270

Ala Leu Lys Glu Ala Val Asp Val Leu Ala Ile Thr Gly Ser Lys
    275                 280                 285

Asp Leu Asn Met Leu Gly Ala Cys Ser Gly Gly Ile Thr Cys Thr Ala
290                 295                 300

Leu Val Gly His Tyr Ala Ala Leu Gly Glu Lys Val Asn Ala Leu
305                 310                 315                 320

Thr Leu Leu Val Ser Val Leu Asp Thr Thr Leu Asp Thr Gln Val Ala
                325                 330                 335

Leu Phe Val Asp Glu Gln Thr Leu Glu Ser Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Ile Thr Arg Leu Pro Ala Ala Phe His Gly Asp Leu Ile Glu Met Phe
                405                 410                 415

Lys Asn Asn Pro Leu Val Arg Pro Gly Ala Leu Glu Val Cys Gly Thr
            420                 425                 430

Pro Ile Asp Leu Ser Gln Val Thr Thr Asp Ile Phe Ser Val Ala Gly
        435                 440                 445

Thr Asn Asp His Ile Thr Pro Trp Lys Ser Cys Tyr Lys Ser Ala Gln
    450                 455                 460

Leu Phe Gly Gly Lys Val Glu Phe Leu Leu Ser Asn Ser Gly His Ile
465                 470                 475                 480

Gln Ser Ile Leu Asn Pro Pro Gly Asn Pro Lys Ser Arg Tyr Met Thr
                485                 490                 495

Ser Ser Glu Met Pro Ala Gln Ala Asp Asp Trp Gln Glu Asn Ser Thr
            500                 505                 510

Lys His Thr Asp Ser Trp Trp Leu Tyr Trp Gln Ala Trp Leu Ala Glu
        515                 520                 525

Arg Ser Gly Ala Leu Lys Pro Ala Pro Ala Lys Leu Gly Asn Lys Ala
    530                 535                 540

Tyr Pro Ser Ala Glu Ala Ser Pro Gly Thr Tyr Val His Glu Arg
545                 550                 555
```

<210> SEQ ID NO 2
<211> LENGTH: 1680
<212> TYPE: DNA
<213> ORGANISM: Pseudomonas putida P91
<220> FEATURE:
<221> NAME/KEY: CDS
<222> LOCATION: (1)...(1680) Polyhydroxyalkanoate synthase encoding sequence

<400> SEQUENCE: 2
atgagtaaca agaacaacga tgacctgcag cgccaagcct ctgaaaacac cctgggcctg     60
agccccatca ttggcctgcg ccgaaaggat ttgctgtctt cggcccggat ggtgctgcgt    120

-continued

```
caggccatca agcaaccgct gcacagtgcc aagcacgtcg cgcatttcgg cctgcagctc      180
aaggacgtga tcttcggcaa gtccggcctg cagccggagg cgacgaccg ccgcttcagc       240
gacccggcct ggagccagaa cccgctgtac cgccgctacc tgcagaccta cctggcctgg     300
cgcaaggaac tgcacgactg gatcggcaac agcaacctgt cggagcagga catcagccgc     360
gcgcacttcg tcatcaacct gatgaccgag gccatggccc caccaacag gcgggccaac      420
ccggcagcgg tcaagcgctt cttcgaaacc ggtggcaaga gcctgctcga cggcctgtcg     480
cacctggcca aggacatggt ccacaacggc ggcatgccca gccaggtcaa catggacgcc     540
ttcgaggtgg gcaagaacct ggccaccacc gagggcgccg tggtatttcg caacgacgtg     600
ctggagctga tccagtaccg cccgatcacc gagcaggtgc acgaaaagcc gctgctggtg     660
gtaccgccgc agatcaacaa gttctacgtc ttcgacctca gcccggaaaa gagcctggcg     720
cgcttctgcc tgcgctccac ggtgcagacc ttcatcgtga gctggcgcaa ccccaacaag     780
tcccagcgca gtggggcct gtcgacctac atcgatgcgc tcaaggaggc cgtcgacgtg      840
gtgctggcaa tcaccggcag caaggacctg aacatgctcg gtgcctgctc cggcggcatc     900
acctgcaccg cgctggtggg ccactacgcg gcactgggcg agaagaaggt caatgccctg     960
accctgctgg tgagcgtgct cgacaccacc ctcgacaccc aggtggcgct gttcgtcgac    1020
gagcagaccc tggagtcggc caagcgccat tcctaccagg ccggtgtgct cgaaggccgc    1080
gacatggcca aggtgttcgc ctggatgcgc cccaacgacc tgatctggaa ctactgggtc    1140
aacaactacc tgctcggcaa cgagccgccg gtgttcgaca tcctgttctg gaacaacgac    1200
atcacgcgcc tgcccgccgc cttccacggc gacctgatcg aaatgttcaa gaacaacccg    1260
ctggtgcgtc ccggtgcact ggaagtgtgc ggcacgccga tcgacctgag ccaggtcacc    1320
accgacatct tcagcgtggc cggcaccaac gatcacatca ccccatggaa gtcctgctac    1380
aagtcggcgc agctgttcgg cggcaaggtc gagttcctgc tgtccaacag cgggcatatc    1440
cagagcatcc tcaacccgcc gggcaacccc aagtcgcgct acatgaccag cagcgagatg    1500
ccggcccagg ccgacgactg gcaggagaac tccaccaagc acaccgattc ctggtggctg    1560
tactggcagg cgtggctggc cgagcgctcc ggcgcactca gccggcacc cgccaagctg    1620
ggcaacaagg cctacccgag cgccgaagcg tcgcccggca cctacgtcca cgaacgctga    1680
```

<210> SEQ ID NO 3
<211> LENGTH: 560
<212> TYPE: PRT
<213> ORGANISM: Pseudomonas putida P91
<220> FEATURE:
<223> OTHER INFORMATION: Polyhydroxyalkanoate synthase

<400> SEQUENCE: 3

```
Met Lys Asp Lys Pro Ala Lys Pro Gly Val Pro Thr Pro Ala Ala Tyr
1               5                   10                  15

Leu Asn Val Arg Ser Ala Ile Ser Gly Leu Arg Gly Arg Asp Leu Leu
                20                  25                  30

Ser Thr Val His Gln Leu Gly Arg His Gly Leu Arg His Pro Leu His
            35                  40                  45

Thr Ala Arg His Leu Leu Ala Leu Gly Gly Gln Leu Gly Arg Val Met
        50                  55                  60

Leu Gly Asp Thr Pro Tyr Gln Pro Ser Pro Arg Asp Thr Arg Phe Asn
65                  70                  75                  80

Asp Pro Ala Trp Gln Leu Asn Pro Leu Tyr Arg Arg Gly Leu Gln Ala
                85                  90                  95
```

-continued

Tyr Leu Ala Trp Gln Gln Gln Thr Cys Gln Trp Ile Asp Glu Ser Gln
        100                 105                 110

Leu Asp Asp Asp Arg Ala Arg Ala His Phe Val Phe Ser Leu Leu
            115                 120                 125

Asn Asp Ala Met Ser Pro Ser Asn Thr Leu Leu Asn Pro Ala Ala Val
        130                 135                 140

Lys Glu Leu Leu Asn Ser Gly Gly Leu Ser Leu Val Arg Gly Leu Asn
145                 150                 155                 160

His Leu Leu Asp Asp Leu Arg His Asn Asp Gly Leu Pro Arg Gln Val
                165                 170                 175

Asn Pro Asp Ala Phe Glu Val Gly Arg Asn Leu Ala Ser Thr Ala Gly
            180                 185                 190

Ala Val Val Phe Arg Asn Glu Leu Glu Leu Ile Gln Tyr Arg Pro
        195                 200                 205

Met Ser Glu Lys Gln Tyr Ala Arg Pro Leu Leu Val Val Pro Pro Gln
        210                 215                 220

Ile Asn Lys Phe Tyr Ile Phe Asp Leu Ser Pro Thr Asn Ser Phe Val
225                 230                 235                 240

Gln Tyr Ala Leu Lys Asn Gly Leu Gln Thr Phe Met Ile Ser Trp Arg
                245                 250                 255

Asn Pro Asp Ala Arg His Arg Glu Trp Gly Leu Ser Ser Tyr Val Ala
            260                 265                 270

Ala Val Glu Glu Ala Met Asn Val Cys Arg Ser Ile Thr Gly Ser Arg
        275                 280                 285

Asp Val Asn Leu Leu Gly Ala Cys Ala Gly Gly Leu Thr Ile Ala Ala
        290                 295                 300

Leu Gln Gly His Leu Gln Ala Lys Arg Gln Met Arg Arg Val His Ser
305                 310                 315                 320

Ala Thr Tyr Leu Val Ser Leu Leu Asp Ser Gln Phe Asp Ser Pro Ala
                325                 330                 335

Ser Leu Phe Ala Asp Glu Gln Thr Leu Glu Ala Ala Lys Arg Arg Ser
            340                 345                 350

Tyr Gln Gln Gly Val Leu Glu Gly Arg Glu Met Ala Arg Val Phe Ala
        355                 360                 365

Trp Met Arg Pro Asn Asp Leu Ile Trp Asn Tyr Phe Val Asn Asn Tyr
        370                 375                 380

Leu Leu Gly Lys Ala Pro Pro Ala Phe Asp Ile Leu Tyr Trp Asn Asn
385                 390                 395                 400

Asp Asn Ser Arg Leu Pro Ala Ala Leu His Gly Asp Leu Leu Asp Phe
                405                 410                 415

Phe Lys Phe Asn Pro Leu Thr His Ala Asp Gly Leu Glu Val Cys Gly
            420                 425                 430

Thr Pro Ile Asp Leu Asn Lys Val Thr Val Asp Ser Phe His Val Ala
        435                 440                 445

Gly Ser Asn Asp His Ile Thr Pro Trp Asp Ala Val Tyr Arg Ser Ala
    450                 455                 460

Leu Leu Leu Gly Gly Glu Arg Arg Phe Val Leu Ala Asn Ser Gly His
465                 470                 475                 480

Val Gln Ser Ile Leu Asn Pro Pro Gly His Pro Lys Ala His Phe Val
                485                 490                 495

Glu Asn Pro Arg Leu Ser Ser Asp Pro Arg Ala Trp Tyr His Asp Ala
            500                 505                 510

-continued

```
Gln Lys Val Glu Gly Ser Trp Trp Pro Gln Trp Leu Asp Trp Ile Gln
        515                 520                 525

Ala Arg Ser Gly Ala Gln Arg Glu Thr Arg Leu Ser Leu Gly Ser Ala
    530                 535                 540

Asn Tyr Pro Pro Met Asp Pro Ala Pro Gly Thr Tyr Val Leu Val Arg
545                 550                 555                 560
```

<210> SEQ ID NO 4
<211> LENGTH: 1683
<212> TYPE: DNA
<213> ORGANISM: Pseudomonas putida P91
<220> FEATURE:
<221> NAME/KEY: CDS
<222> LOCATION: (1)...(1683) Polyhydroxyalkanoate synthase encoding sequence

<400> SEQUENCE: 4

| | | | | | |
|---|---|---|---|---|---|
| atgaaagaca | agcccgcgaa | gcccggggta | ccgaccccg | ctgcctatct | caacgtgcgc | 60 |
| agcgccatca | gtggcctgcg | cggtcgcgac | ctgctgtcga | cggtgcacca | gctggggcgc | 120 |
| cacggcctgc | gtcacccgct | gcacacggcg | cgccacctgc | tggcgctggg | tggccagctg | 180 |
| ggcgcgtga | tgctgggcga | taccccctac | cagccctcgc | cacgcgacac | ccgcttcaac | 240 |
| gacccggcct | gcagctcaa | cccgctgtac | cgacgcggcc | tgcaggccta | cctggcctgg | 300 |
| cagcagcaga | cctgccagtg | gatcgacgag | agccagctgg | acgacgatga | ccgcgcccgc | 360 |
| gcgcacttcg | tgttctcgct | gctcaacgat | gcaatgtcgc | ccagcaacac | cctgctcaac | 420 |
| ccggcggcg | tcaaggagct | gctgaactcc | ggcgggctga | gctggtgcg | cggcttgaac | 480 |
| cacctgctcg | acgacctgcg | ccacaacgac | ggcctgccac | gccaggtcaa | cccggacgcc | 540 |
| ttcgaggtgg | gcaggaacct | ggccagcacc | gccggcgcgg | tggtgtttcg | caacgagctg | 600 |
| ctggagctga | tccagtaccg | cccgatgagc | gaaaaacagt | acgcccggcc | cctgctggtg | 660 |
| gtgccgccgc | agatcaacaa | gttctacatc | ttcgacctca | gcccgaccaa | cagctttgtg | 720 |
| cagtacgccc | tcaagaacgg | cctgcagacc | ttcatgatca | gctggcgcaa | ccccgacgcc | 780 |
| cggcatcgcg | aatggggcct | gtcgagctac | gtggcggcgg | tcgaggaagc | catgaacgtg | 840 |
| tgccgctcga | tcaccggcag | ccgcgacgtc | aacctgcttg | gcgcctgtgc | cggcgggttg | 900 |
| accatcgcgg | ccctgcaggg | tcacctgcag | gccaagcgcc | agatgcgccg | ggtgcacagc | 960 |
| gccacctacc | tggtcagcct | gctcgacagc | cagttcgaca | gccccgccag | cctgttcgcc | 1020 |
| gacgagcaga | ccctggaggc | ggccaagcgc | gctcctacc | agcagggcgt | gctggagggc | 1080 |
| cgcgagatgg | cacgggtgtt | cgcctggatg | cgccccaacg | acctgatctg | gaactacttc | 1140 |
| gtcaacaact | acctgctggg | caaggcgccc | ccggcattcg | acatcctgta | ctggaacaac | 1200 |
| gacaacagcc | gcctgccggc | cgcgctgcac | ggcgatctgc | tggacttctt | caaattcaac | 1260 |
| ccgctgacgc | acgccgacgg | cctcgaggta | tgcggcacgc | cgatcgacct | gaacaaggtc | 1320 |
| acggtggaca | gcttccacgt | ggccggcagc | aacgaccaca | tcaccccgtg | ggacgcggtg | 1380 |
| taccgctcgg | ccctgctgct | gggcggcgag | cggcgcttcg | tgctggccaa | cagcgggcat | 1440 |
| gtgcagagca | tcctcaaccc | accgggccac | cccaaggcgc | attttgtcga | aaccccagg | 1500 |
| ctgagcagcg | accgcgggc | ctggtaccac | gatgcgcaga | aggtcgaggg | cagctggtgg | 1560 |
| ccgcagtggc | tcgactggat | acaggcgcgc | tccggtgcgc | agcgcgaaac | ccgcctgtcg | 1620 |
| ctgggcagcg | ccaattaccc | tcccatggac | cccgcacccg | gcacctacgt | gctggtgcgc | 1680 |
| tga | | | | | | 1683 |

```
<210> SEQ ID NO 5
<211> LENGTH: 20
<212> TYPE: DNA
<213> ORGANISM: Artificial Sequence
<220> FEATURE:
<223> OTHER INFORMATION: Probe sequence

<400> SEQUENCE: 5
tgctggaact gatccagtac                                              20

<210> SEQ ID NO 6
<211> LENGTH: 23
<212> TYPE: DNA
<213> ORGANISM: Artificial Sequence
<220> FEATURE:
<223> OTHER INFORMATION: Probe sequence

<400> SEQUENCE: 6
gggttgagga tgctctggat gtg                                          23

<210> SEQ ID NO 7
<211> LENGTH: 30
<212> TYPE: DNA
<213> ORGANISM: Artificial Sequence
<220> FEATURE:
<223> OTHER INFORMATION: Primer sequence for PCR

<400> SEQUENCE: 7
cagccaagct tgtactcgtc tcaggacaac                                   30

<210> SEQ ID NO 8
<211> LENGTH: 29
<212> TYPE: DNA
<213> ORGANISM: Artificial Sequence
<220> FEATURE:
<223> OTHER INFORMATION: Primer sequence for PCR

<400> SEQUENCE: 8
agagataagc ttgcggcatg cgcgagccc                                    29

<210> SEQ ID NO 9
<211> LENGTH: 30
<212> TYPE: DNA
<213> ORGANISM: Artificial Sequence
<220> FEATURE:
<223> OTHER INFORMATION: Primer sequence for PCR

<400> SEQUENCE: 9
cattgaagct ttggttgatg gcctgacgac                                   30

<210> SEQ ID NO 10
<211> LENGTH: 29
<212> TYPE: DNA
<213> ORGANISM: Artificial Sequence
<220> FEATURE:
<223> OTHER INFORMATION: Primer sequence for PCR

<400> SEQUENCE: 10
ctccaagctt cggtcgcggg tcttcatcc                                    29
```

POLYHYDROXYALKANOATE SYNTHASE AND GENE ENCODING THE SAME

This application is a continuation-in-part of application Ser. No. 09/820,721, filed Mar. 30, 2001 now abandoned.

BACKGROUND OF THE INVENTION

1. Field of the Invention

This invention relates to a polyhydroxyalkanoate (hereinafter, referred to as a "PHA") synthase, a gene encoding the synthase, a recombinant vector containing the gene, a transformant transformed by the vector, a process for producing the PHA synthase utilizing the transformant, and a process for preparing the PHA utilizing the transformant.

2. Related Background Art

There have been reported a number of microorganisms producing poly-3-hydroxybutyric acid (PHB) or another PHA and storing it therein ("Biodegradable Plastic Handbook", edited by Biodegradable Plastic Research Society, NTS Co. Ltd., p. 178–197 1995). These polymers may be, as conventional plastics, used for producing a variety of products by, for example, melt processing. Since they are biodegradable, they have an advantage that they can be completely degraded by microorganisms in the natural environment, and they do not cause pollution due to remaining in the natural environment like many conventional polymer compounds. Furthermore, they are excellently biocompatible, and thus are expected to be used in applications such as a medical soft member.

It is known that a composition and a structure of such a PHA produced by a microorganism may considerably vary depending on the type of a microorganism used for the production, a culture-medium composition and culturing conditions. Investigations have been, therefore, mainly focused on controlling such a composition or structure for the purpose of improving physical properties of a PHA.

For example, Japanese Patent Application Nos. 7-14352 and 8-19227 and Japanese Examined Publication No. 6-15604 describe that *Alcaligenes eutropus* H16 (ATCC No. 17699) and its variants may produce 3-hydroxybutyric acid (3HB) and its copolymer with 3-hydroxyvaleric acid (3HV) with various composition ratios by changing a carbon source during culturing.

Japanese Patent Publication No. 2642937 has disclosed that PHA in which a monomer unit is 3-hydroxyalkanoate with 6 to 12 carbon atoms may be produced by supplying a non-cyclic aliphatic hydrocarbon as a carbon source to *Pseudomonas oleovorans* (ATCC No. 29347).

Japanese Patent Application Laid-Open No. 5-7492 discloses methods in which *Methylobacterium* sp., *Paracoccus* sp., *Alcaligenes* sp., and *Pseudomonas* sp. are contacted with a primary alcohol with 3 to 7 carbon atoms to produce a copolymer of 3HB and 3HV.

Japanese Patent Application Laid-Open No. 5-93049 and No. 7-265065 have disclosed that *Aeromonas caviae* is cultured using oleic acid or olive oil as a carbon source to produce a two-component copolymer of 3HB and 3-hydroxyhexanoic acid (3HHx).

Japanese Patent Application Laid-Open No. 9-191893 has disclosed that *Comamonas acidovorans* IF013852 is cultured using gluconic acid and 1,4-butanediol as carbon sources to produce a polyester having 3HB and 4-hydroxybutyric acid as monomer units.

Furthermore, it has been reported that certain microorganisms produce PHAs having a variety of substituents such as groups derived from an unsaturated hydrocarbon, ester, allyl, cyano, groups derived from a halogenated hydrocarbon and epoxide. Recently, there have been attempts for improving physical properties of a PHA produced by a microorganism using such a procedure.

As an example of such a polymer, a PHA having a phenyl group in its side chain has been developed. For example, Makromol Chem., 191, 1957–1965 (1990); Macromolecules, 24, 5256–5260 (1991); and Chirality, 3, 492–494 (1991) have described production of a PHA comprising 3-hydroxy-5-phenylvaleric acid (3HPV) as a monomer unit by *Pseudomonas oleovorans*, where there has been observed variation in polymer physical properties probably due to the presence of 3HPV.

As described above, microorganism-produced PHAs with various combinations of composition and structure have been obtained by varying factors such as the type of a microorganism used, a culture medium composition and culturing conditions. However, each microorganism or PHA synthase has significantly different substrate specificity. Therefore, it has been difficult to produce PHAs comprising different monomer units extensively suitable to a variety of applications using known microorganisms or PHA synthases alone.

SUMMARY OF THE INVENTION

A PHA having a substituent in its side chain as described above may be expected to be a "functional polymer" having significantly useful functions and properties owing to the properties of the introduced substituent. It is, therefore, extremely useful and important to prepare a gene encoding a PHA synthase from a microorganism which can produce and store a very useful polymer having both such functionality and biodegradability; prepare a recombinant vector comprising the gene, a transformant transformed by the vector; and develop a process for producing a PHA synthase utilizing the transformant and a process for preparing a PHA utilizing the transformant.

In view of usefulness of such a PHA synthase useful in PHA production, an object of the present invention is to provide a PHA synthase, a gene encoding the enzyme, a recombinant vector comprising the gene, a transformant transformed by the vector, a process for producing a PHA synthase utilizing the transformant and a process for preparing a PHA utilizing the transformant.

For developing a PHA having a novel side-chain structure useful as, for example, a device material or a medical material, the inventors have searched a novel microorganism capable of producing and storing the desired PHA. Additionally, the inventors have intensely investigated for preparing a gene encoding a PHA synthase from such a microorganism, a recombinant vector containing the gene, a transformant transformed by the vector and developing a process for producing a PHA synthase utilizing the transformant and a process for preparing a PHA utilizing the transformant.

The inventors have finally found a novel microorganism capable of producing and storing a novel PHA comprising 3-hydroxy-5-(4-fluorophenyl)valeric acid (3HFPV) represented by formula (2) as a monomer unit from synthetic 5-(4-fluorophenyl)valeric acid (PPVA) represented by formula (1) as a starting material, and designate it as P91 strain.

[General formula (1)]

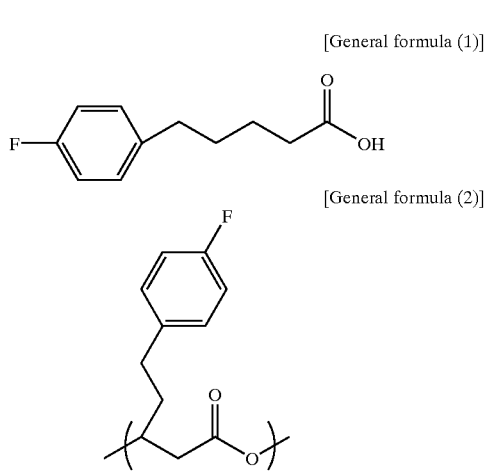

[General formula (2)]

The inventors have also found that P91 strain in capable of producing and storing a PHA comprising 3-hydroxy-4-phenoxy-n-butyric acid (3HPxB) represented by formula (4) as a monomer unit from 4-phenoxy-n-butyric acid (PxBA) represented by formula (3) as a starting material.

[General formula (3)]

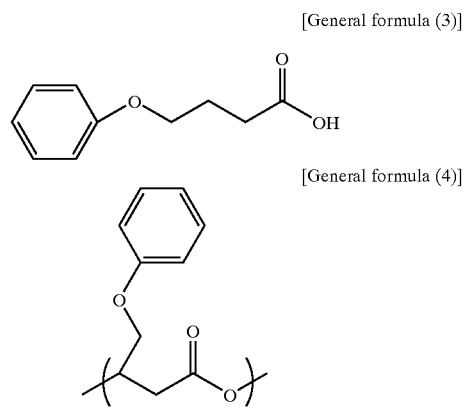

[General formula (4)]

An example of a microorganism capable of producing and storing a PHA comprising 3HPxB as a monomer unit is *Pseudomonas oleovorans* involved in a process described in Macromolecules. 29, 3432–3435, 1996. This process is considerably different from the process using PxBA as a substrate in P91 strain in that 8-phenoxyoctanoic acid (PxOA) is used as a substrate. In addition, for a PHA produced, the above reported process provides a copolymer consisting of three monomer units, i.e., 3-hydroxy-8-phenoxyoctanoic acid derived from the substrate PxOA, 3-hydroxy-6-phenoxyhexanoic acid as a byproduct derived from a metabolite and 3HPxB. On the other hand, P91 strain can produce a PHA comprising 3HPxB derived from PxBA as a sole phenoxy-containing monomer unit. In this respect, P91 strain is basically different from the above reported strain.

There are no reports describing microbial production of a PHA comprising 3HPxD as a monomer unit using PxBA as a substrate or 3HPxB as a sole phenoxy-containing monomer unit.

Microbiological properties of P91 strain according to this invention are as follows.
<Microbiological Properties of P91 Strain>
(Morphologic Properties)
Cell shape and size: Bacilliform, 0.6 μm×1.5 μm
Cell polymorphism: No
Motility: Yes
Sporulation: No
Gram stainability: Negative
Colonization: Circular, smooth in the overallperiphery, low convex, smooth surface, gloss, cream color
(Physiological Properties)
Catalase: Positive
Oxidase: Positive
O/F test: oxidized form
Reduction of a nitrate: Negative
Indole formation: Negative
Acidification of dextrose: Negative
Arginine dihydrolase: Positive
Urease: Negative
Esculin hydrolysis: Negative
Gelatin hydrolysis: Negative
β-Galactosidase: Negative
Fluorochrome production on King's B agar: Positive
(Substrate Assimilation Ability)
Dextrose: Positive
L-Arabinose: Negative
D-Mannose: Negative
D-Mannitol: Negative
N-Acetyl-D-glucosamine: Negative
Maltose: Negative
Potassium gluconate: Positive
n-Capric acid: Positive
Adipic acid: Negative
dl-Malic acid: Positive
Sodium citrate: Positive
Phenyl acetate: Positive From these microbiological properties, the inventors have attempted to categorize P91 strain according to Bergey's Manual of Systematic Bacteriology, Volume 1 (1984) and Bergey's Manual of Determinative Bacteriology 9th ed. (1994) to determine that the strain belongs to *Pseudomonas putida*. Thus, the strain was designated as *Pseudomonas putida* P91. The inventors have deposited *Pseudomonas putida* P91 to Patent Microorganism Depository Center in the National Institute of Bioscience and Human Technology, Agency of Industrial Science and Technology, Ministry of International Trade and Industry, under the deposition number of FERM P-17409. P91 strain has been internationally deposited on the basis of the Budapest Treaty, and its international deposition number is "FERM BP-7373".

The inventors have intensely conducted investigation for solving the above problems and finally have succeeded cloning a gene for a PHA synthase from P91 strain to achieve this invention.

Specifically, a PHA synthase of this invention is characterized in that it has the amino acid sequence of SEQ ID NO.:1 or 3. A PHA synthase according to the present invention may include a mutant PHA synthase where at least one mutation including deletion, substitution or addition of at least one amino acid is introduced as long as it does not deteriorate PHA synthase activity exhibited by a protein comprising these amino acid sequences.

The present invention also encompasses a PHA synthase gene coding a PHA synthase comprising the amino acid sequence of SEQ ID NO.:1 or 3. Examples of a sequence of such a gene include SEQ ID NO.:2 or 4. Furthermore, a mutant PHA synthase gene encoding the above mutant PHA synthase obtained by mutation of the sequence of SEQ ID NOs.:2 and 4 is included in a PHA synthase gene according to this invention.

The present invention also encompasses a recombinant vector comprising the above PHA synthase gene and a transformant transformed by the recombinant vector. The present invention also encompasses a process for producing a PHA synthase comprising the steps of culturing the transformant and isolating the PHA synthase from a culture obtained, and a process for preparing a PHA comprising the steps of culturing the transformant and isolating the PHA from a culture obtained.

The present invention provides a PHA synthase, a gene encoding the PHA synthase, a recombinant vector comprising the gene and a transformant transformed by the recombinant vector. The PHA synthase gene according to the present invention is useful for preparing a PHA having various physical properties because it encodes a PHA synthase using a monomer having a novel side-chain structure as a substrate.

DETAILED DESCRIPTION OF THE PREFERRED EMBODIMENTS

The present invention will be more detailed. A PHA synthase gene of the present invention is isolated from *Pseudomonas putida* P91 strain. First, a chromosome DNA is obtained from a strain having a PHA synthase gene. The chromosome DNA may be isolated by a known technique.

For example, after P91 strain is cultured in a LB medium or an M9 medium supplemented with an appropriate carbon source, a chromosome DNA is prepared as described by, for example, Marmer et al. in Journal of Molecular Biology, Vol. 3. p. 208 (1961). The chromosome DNA thus obtained is digested using an appropriate restriction enzyme (e.g., Sau3AI) and a fragment with a proper length is ligated with a ligatable vector digested with a restriction enzyme (e.g., BamHI) to prepare a gene library. Herein, a proper fragment length varies, e.g., about 4000 to 25000 bps for a usual plasmid vector and about 15000 to 30000 bps for a cosmid or phage vector. A proper length of DNA fragment may be collected by a known method such as a method using a sucrose density gradient or using an agarose gel described in Molecular Cloning, Cold Spring Harbor Laboratory (1982).

A vector is a phage vector or plasmid vector which can autonomously replicate in the host microorganism. Examples of phage or cosmid vectors include pWE15, M13, λEMBL3, λEMBL4, λFIXII, λDASHII, λZAPII, λgT10, λgt11, Charon4A and Charon21A. Examples of plasmid vectors include pBR, pUC, pBluescriptII, pGEM, pTZ and pET groups. Various shuttle vectors may be used, e.g., vectors which may autonomously replicate in a plurality of host microorganisms such as *E. coli* and *Pseudomonas* sp. These vectors may be also digested with a proper restriction enzyme to provide a desired fragment as described above.

A chromosome DNA fragment may be ligated with a vector fragment using a DNA ligase. For example, a ligation kit (Takara Shuzo Co., Ltd., etc.) may be used. Thus, for example, a chromosome DNA fragment may be ligated with a vector fragment to prepare a mixture of recombinant plasmids comprising various DNA fragments (hereinafter, referred to as a "gene library"). In addition to a method using a proper length of chromosome DNA fragment, a gene library may be prepared by a method that mRNAs are extracted from P91 strain, purified and used for preparation of a cDNA fragment using a reverse transcriptase as described in Molecular Cloning, Cold Spring Harbor Laboratory, 1982. Alternatively, a gene library is transformed or transduced to *E. coli*, and then the gene library may be amplified to a large amount as described in Molecular Cloning, Cold Spring Harbor Laboratory, 1982.

A recombinant vector may be introduced into a host microorganism by a known method. For example, when using *E. coli* as a host microorganism, a calcium chloride method (Journal of Molecular Biology, Vol. 53, p. 159 (1970)), a rubidium chloride method (Methods in Enzymology, Vol. 68, p. 253 (1979)), electroporation (Current Protocols in Molecular Biology, Vol. 1, p. 184 (1994)) may be used. When using a cosmid vector or phage vector, transduction may be conducted using in vitro packaging (Current Protocols in Molecular Biology, Vol. 1, p. 571 (1994)). Alternatively, a method involving conjugational transfer may be used.

Then, a probe is prepared for obtaining a DNA fragment comprising a PHA synthase gene of P91 strain.

Some base sequences have been reported for PHA synthase genes; for example, Peoples, O. P. and Sinskey, A. J., J. Biol. Chem. 264, 15293 (1989); Huisman, G. W. et al., J. Biol. Chem., 266, 2191 (1991); Pieper, U. et al., FEMS Microbiol. Lett., 96, 73 (1992); Timm, A. and Steinbuchel, A., Eur. J. Biochem., 209, 15(1992); Matsusaki. H. et al., J. Bacteriol., 180, 6459 (1998).

From these reported sequences, a region where a sequence is preserved to a higher degree is selected for designing an oligonucleotide. Such an oligonucleotide includes, but not limited to, a sequence described in Timm, A. and Steinbuchel, A., Eur. J. Biochem., 209, 15 (1992). An oligonucleotide may be synthesized using, for example, Custom Synthesis Service, Amersham-Pharmacia Biotech.

Then, the designed oligonucleotide as a primer is subject to polymerase chain reaction (hereinafter, referred to as "PCR") using a chromosome DNA in P91 strain as a template to partially amplify the PHA synthase gene. The PCR amplified fragment thus obtained is homologous to the PHA synthase gene of P91 strain to about 100%, and may be expected to give a higher S/N ratio as a probe during colony hybridization and may allow stringency control in hybridization to be facilitated. The above PCR amplified fragment is labeled with an appropriate reagent and used for colony-hybridization of the above chromosome DNA library to select a PHA synthase gene (Current Protocols in Molecular Biology, Vol. 1, p. 603 (1994)). The PCR amplified fragment may be labeled using a commercially available kit such as AlkPhosDirect (Amersham-Pharmacia Biotech).

A gene fragment comprising a PHA synthase gene may be selected by, in addition to the above method using a genotype, a method using a phenotype where PHA synthesis is directly evaluated. The presence of PHA synthesis may be detected by, for example, staining with Sudan Black B (Archives of Biotechnology. VOl. 71, p. 283 (1970)) or determination of PHA accumulation by phase contrast microscopy.

A plasmid may be collected from *E. coli* selected by any of the above methods using an alkali method (Current Protocols in Molecular Biology, Vol. 1, p. 161 (1994)) to obtain a DNA fragment comprising a PHA synthase gene. The DNA fragment obtained may be sequenced by, for example, Sanger's sequencing method (Molecular Cloning, Vol. 2, p. 133 (1989). Alternatively, it may be conducted by a dye-primer method or a dye-terminator method using an automatic sequencer such as DNA Sequencer 377A (Perkin Elmer).

After determining all the sequences, hybridization may be conducted using a DNA fragment prepared by an appropriate method, such as chemical synthesis, PCR using a chromosome DNA as a template, or digestion of a DNA fragment comprising the sequence with a restriction enzyme as a probe, to provide a gene of this invention.

SEQ ID NOs.:2 and 4 show the sequences of PHA synthase gene of this invention while SEQ ID NOs.:1 and 3 show the amino acid sequences coded by the genes. As described above, there may be mutations for one or several amino acids such as deletion, substitution or addition as long as the polypeptides having these amino acid sequences retain PHA producing activity. In addition to those having the sequence coding the amino acids of SEQ ID NOs.:1 and 3, the present invention may include a degenerated isomer coding the same polypeptide which has the same amino acid sequence and is different only in a degeneration codon. Mutation such as deletion, substitution and addition may be introduced by, e.g., a site mutation introduction technique (Current Protocols in Molecular Biology Vol. 1, p. 811 (1994)).

A transformed microorganism of this invention may be produced by introducing a recombinant vector of the present invention into a host suitable to an expression vector used during preparing the recombinant vector. Examples of microorganisms which may be used as a host include various bacteria such as *Esherichia* sp., *Pseudomonas* sp., *Ralstonia* sp., *Alcaligenes* sp., *Comamonas* sp., *Burkholderia* sp., *Agrobacterium* sp., *Plabobacterium* sp., *Vibrio* sp., *Enterobacter* sp., *Rhizobium* sp., *Gluconobacter* sp., *Acinetobacter* sp., *Moraxella* sp., *Nitrosomonas* sp., *Aeromonas* sp., *Paracoccus* sp., *Bacillus* sp., *Clostridium* sp., *Lactobacillus* sp., *Coryncbacterium* sp., *Artbrobacter* sp., *Achromobacter* sp., *Micrococcus* sp., *Mycobacterium* sp., *Streptococcus* sp., *Streptomyces* sp., *Actinomyces* sp., *Norcadia* sp. and *Methylobacterium* sp. Besides the above bacteria, yeasts and molds such as *Saccharomyces* sp. and *Candida* sp. may be used as a host.

When using a microorganism belonging to *Pseudomonas* sp., e.g., a bacterium such as *E. coli* as a host, it is preferable that the recombinant vector of the present invention itself can autonomously replicate in a host used while comprising a constitution required for expression such as a promoter, a DNA comprising a PHA synthase gene and a transcription termination sequence. Expression vectors include pLA2917 (ATCC 37355) having a RK2 replication origin which may be replicated and retained by a range of hosts or pJRD215 (ATCC 37533) having a RSF1010 replication origin, but any vector having a replication origin which may be replicated and retained by a wide range of hosts may be used.

Any promoter which may be expressed in a host may be used; for example, promoters derived from *E. coli*, a phage, etc. such as trp. trc, tac, lac, PL, PR, T7 and T3 promoters. A recombinant DNA may be introduced in a bacterium by an appropriate procedure such as the above calcium chloride method and electroporation.

When using a yeast as a host, an expression vector may be YEp13, YCp50, pRs or pYEX vector. A promoter may be, for example, GAL or AOD promoter. A recombinant DNA may be introduced into an yeast by, for example, electroporation (Methods Enzymol., 194, 182–187 (1990)), a spheroplast method (Proc. Natl. Acad. Sci. USA, 84, 1929–1933 (1978)) and a lithium acetate method (J. Bacteriol., 153, 163–168 (1983)).

A recombinant vector may further have a fragment for expressional regulation which has a variety of functions for suppression, amplification or triggering of expression; a marker for selection of a transformant; a resistance gene to an antibiotic; or a gene encoding a signal for extracellular secretion.

A PHA synthase of the present invention may be prepared by culturing a transformant prepared by transforming a host with a recombinant vector having a gene encoding the synthase to produce and accumulate a PHA synthase as a gene product in the culture (cultured bacterium or culture supernatant) and isolating the PHA synthase from the culture.

The transformant of the present invention may be cultured by a common process used for culturing a host.

Culturing may be conducted by any of common microorganism culturing processes such as batch, flow batch, continuous culturing and reactor styles.

For a transformant obtained using a bacterium such as *E. coli* as a host, a medium used for culturing may be a complete medium or synthetic medium such as LB medium and M9 medium. A microorganism may be grown by aerobically culturing it at a culturing temperature of 25 to 37° C. for 8 to 72 hours to accumulate a PHA synthase in bacterial cells, and the enzyme may be collected. Microbial growth requires a carbon source including sugars such as glucose, fructose, sucrose, maltose, galactose and starches; lower alcohols such as ethanol, propanol and butanol; polyalcohols such as glycerol; organic acids such as acetic acid, citric acid, succinic acid, tartaric acid, lactic acid and gluconic acid; and aliphatic acids such as propionic acid, butanoic acid, pentanoic acid, hexanoic acid, heptanoic acid, octanoic acid, nonanoic acid, decanoic acid, undecanoic acid and dodecanoic acid.

Examples of a nitrogen source include ammonia; ammonium salts such as ammonium chloride, ammonium sulfate and ammonium phosphate; and natural product derivatives such as peptone, meat extract, yeast extract, malt extract, casein decomposition products and corn steep liquor. Examples of an inorganic material include potassium dihydrogen phosphate, potassium monohydrogen phosphate, magnesium phosphate, magnesium sulfate and sodium chloride. The culture medium may contain an antibiotic such as kanamycin, ampicillin, tetracyclin, chloramphenicol and streptomycin.

When culturing a microorganism transformed using an expression vector having an inducible promoter, a proper inducer suitable to the type of the promoter may be added to a culture medium. For example, the inducer may be isopropyl-β-D-thiogalactopyranoside (IPTG), tetracyclin or indoleacrylic acid (IAA).

A PHA synthase may be separated and purified by centrifuging and collecting cells or a supernatant from a culture obtained and processing it by a technique such as cell disruption extraction, affinity chromatography, cation or anion exchange chromatography and gel filtration alone or in combination as appropriate. Whether a purified material is a desired enzyme may be determined by a usual method such as SDS polyacrylamide gel electrophoresis and Western blotting.

The present invention is not limited to the procedures as described above for culturing of a transformant using microorganism as a host, production of a PHA synthase by the transformant and accumulating it in microorganisms, and collection of the PHA synthase from the cells.

When culturing a transformant using a microorganism as a host for PHA production, the procedure may also be used in which the transformant is cultured using an appropriate medium composition and culturing conditions depending on factors such as the host used and the constitution of a recombinant vector introduced in the host and the PHA is obtained from the culture. A medium or culturing conditions may be the same as those illustrated for the above preparation of a PHA synthase.

A PHA may be collected from cells most conveniently by extraction with an organic solvent such as chloroform as usual, but in an environment where using an organic solvent such as chloroform is undesirable, the culture way be treated by a surfactant such as SDS, an enzyme such as lysozyme, or an agent such as EDTA, sodium hypochlorite and ammonia to remove bacterium components other than the PHA for collecting the PHA.

The present invention is not limited to the above procedures for culturing of a transformant using a microorganism as a host, production of a PHA by and accumulation thereof in the transformant, and collection of the PHA from the cells.

EXAMPLES

The present invention will be more specifically described with reference to Examples although these Examples do not limit the technical range of this invention.

Example 1

Cloning of a PHA Synthase Gene of P91 Strain

P91 strain was cultured in 100 mL of LB medium (1% polypeptone, 0.5% yeast extract, 0.5% sodium chloride, pH 7.4) at 30° C. overnight and then a chromosome DNA was separated and collected as described by Marmer. The chromosome DNA obtained was completely digested using a restriction enzyme BglII. A vector pUC18 was cleaned with a restriction enzyme BamHI. After dephosphorylation of the terminals (Molecular Cloning, Vol. 1, p. 572 (1989), Cold Spring Harbor Laboratory), the digested vector and the chromosome DNA fragment after BglII complete digestion were ligated using a DNA ligation kit Ver. II (Takara Shuzo Co., Ltd.). The ligated DNA fragment was used to transform *Escherichia coli* HB101 strain for preparing a chromosome DNA library for P91 strain.

Then, in order to select a DNA fragment comprising a PHA synthase gene of P91 strain, a probe was prepared. An oligonucleotide consisting of the sequences of SEQ ID NOs.:5 and 6 (Amersham-Pharmacia Biotech) was prepared and used as a primer for PCR. An amplified fragment was used as a probe. Labeling of the probe was conducted using AlkPhosDirect (Amersham-Pharmacia Biotech). The probe thus obtained was used to select an *E. coli* strain containing a recombinant plasmid comprising the PHA synthase gene from the chromosome DNA library of P91 strain by colony hybridization. From the selected strain, the plasmid was collected by an alkali method to prepare a DNA fragment comprising a PHA synthase gene.

The gene fragment thus obtained was recombined in a vector pBBR122 (Mo Bi Tec) comprising a wide host range of replication region which did not belong to IncP, IncQ or IncW in an incompatible group. The recombinant plasmid was transformed in *Pseudomonas putida* P91ml strain (a strain depleted of PHA synthesizing ability) by electroporation, and then the P91ml strain regained PHA synthesizing ability and exhibited complementarity.

The fragment comprising a PHA synthase gene was sequenced by Sanger's sequencing method. It was thus found that the fragment comprised a PHA synthase gene having the sequences of SEQ ID NOs.: 2 and 4. SEQ ID NOs.: 1 and 3 show the amino acid sequences coded by SEQ ID NOs.: 2 and 4, respectively.

Example 2

Recombination of a PHA Synthase Gene of P91 Strain to an Expression Vector

An oligonucleotide having a sequence around the initiation codon of the PHA synthase gene of SEQ ID NO.:2 (SEQ ID NO.:7) and an oligonucleotide having a sequence around the termination codon (SEQ ID NO.:8) were designed and synthesized (Amersham-Pharmacia Biotech). The oligonucleotides were used as a primer for PCR to amplify the whole length of the PHA synthase gene (LA-PCR kit; Takara Shuzo Co., Ltd.).

An oligonucleotide having a sequence around the initiation codon of the PHA synthase gene of SEQ ID NO.:4 (SEQ ID NO.:9) and an oligonucleotide having a sequence around the termination codon (SEQ ID NO.:10) were designed and synthesized (Amersham-Pharmacia Biotech). The oligonucleotides were used as a primer for PCR to amplify the whole length of the PHA synthase gene (LA-PCR kit; Takara Shuzo Co., Ltd.).

Each of the obtained PCR amplified fragments was completely digested using a restriction enzyme HindIII, and ligated to an expression vector pTrc99A which had been truncated with a restriction enzyme HindIII and dephosphorylated (Molecular Cloning, Vol. 1, p. 5.7.2 (1989), Cold Spring Harbor Laboratory), using a DNA ligation kit Ver. II (Takara Shuzo Co., Ltd.).

Using the recombinant plasmids, *Escherichia coli* HB101 was transformed by a calcium chloride method (Takara Shuzo Co., Ltd.), and recombinant plasmids collected from the transformants were designated as pP91-C1 (derived from SEQ ID NO.:2) and pP91-C2 (derived from SEQ ID NO.:4), respectively.

Example 3

PHA Production (1) Using a PHA Synthase Gene Recombinant *E. coli*

Using the recombinant plasmids obtained in Example 2, pP91-C1 (derived from SEQ ID NO.:2) and pP91-C2 (derived from SEQ ID NO.:4), an *Escherichia coli* HB101fB (fadB deficient strain) was transformed by a calcium chloride method to prepare recombinant *E. coli* strains derived from the recombinant plasmids, respectively.

Each of the pP91-C1 and pP91-C2 recombinant strains was inoculated to 200 mL of M9 medium containing 0.5% yeast extract and 0.1% FPVA, and the medium was shaken at 37° C. with a rate of 125 strokes/min. After 24 hours, the cells were collected by centrifugation, washed once with cold methanol and lyophilized.

The lyophilized pellet was suspended in 100 mL of chloroform and the suspension was stirred at 60° C. for 20 hours to extract a PHA. After filtering the extract through a membrane filter with a pore size of 0.45 µm, the filtrate was concentrated by rotary evaporation. Then, the concentrate was re-suspended in cold methanol and the precipitate was collected and dried in vacuo to provide a PHA. The PHA thus obtained was subject to methanolysis as usual and analyzed using a gas chromatography-mass spectrometry apparatus (GC-MS, Shimazu QP-5050, EI technique) to identify methyl-esterified PHA monomer units. The results are shown in Table 1.

TABLE 1

|  | pP91-C1 recombinant strain | pP91-C2 recombinant strain |
| --- | --- | --- |
| Cell dry weight | 810 mg/L | 800 mg/L |
| Polymer dry weight | 24 mg/L | 23 mg/L |
| Polymer dry weight/Cell dry weight | 3% | 3% |

TABLE 1-continued

|  | pP91-C1 recombinant strain | pP91-C2 recombinant strain |
|---|---|---|
| Monomer unit composition (area ratio) | | |
| 3-Hydroxybutyric acid | 0% | 0% |
| 3-Hydroxyvaleric acid | 0% | 0% |
| 3-Hydroxyhexanoic acid | 0% | 0% |
| 3-Hydroxyheptanoic acid | 5% | 3% |
| 3-Hydroxyoctanoic acid | 4% | 5% |
| 3-Hydroxynonanoic acid | 9% | 11% |
| 3-Hydroxydecanoic acid | 10% | 12% |
| 3-Hydroxy-5-(4-fluorophenyl)valeric acid | 72% | 69% |

Example 4

PHA Production (2) Using a PHA Synthase Gene Recombinant E. coli

Each of the pP91-C1 and pP91-C2 recombinant strains was inoculated to 200 mL of M9 medium containing 0.5% yeast extract and 0.2% PxBA, and then cultured with shaking at 37° C. with a rate of 125 strokes/min. After 24 hours, the cells were collected by centrifugation, washed once with cold methanol and lyophilized.

The lyophilized pellet was suspended in 100 mL of chloroform and the suspension was stirred at 60° C. for 20 hours to extract a PHA. After filtering the extract through a membrane filter with a pore size of 0.45 μm, the filtrate was concentrated by rotary evaporation. Then, the concentrate was re-suspended in cold methanol and only the precipitant was collected and dried in vacuo to provide a PHA. The PHA thus obtained was subject to methanolysis as usual and analyzed using a gas chromatography-mass spectrometry apparatus (GC-Ms, Shimazu QP-5050, EI technique) to identify methyl-esterified PHA monomer units. The results are shown in Table 2.

TABLE 2

|  | pP91-C1 recombinant strain | pP91-C2 recombinant strain |
|---|---|---|
| Cell dry weight | 750 mg/L | 720 mg/L |
| Polymer dry weight | 4 mg/L | 4 mg/L |
| Polymer dry weight/Cell dry weight | 0.5% | 0.6% |
| Monomer unit composition (area ratio) | | |
| 3-Hydroxybutyric acid | 0% | 0% |
| 3-Hydroxyvaleric acid | 0% | 0% |
| 3-Hydroxyhexanoic acid | 0% | 0% |
| 3-Hydroxyheptanoic acid | 2% | 2% |
| 3-Hydroxyoctanoic acid | 3% | 3% |
| 3-Hydroxynonanoic acid | 5% | 7% |
| 3-Hydroxydecanoic acid | 5% | 6% |
| 3-Hydroxy-4-phenoxy-n-butyric acid | 85% | 82% |

Example 5

Homology of a PHAsynthase Gene of P91 Strain

In the same manner as in Example 1, the chromosome DNA of P91 strain was separated and collected. Further, Pseudomonas olevorans ATCC29347, Pseudomonas putida Tk2440 and Pseudomonas aeruginose PA01 were cultured and the chromosome DNAs thereof were separated and collected in the same as in Example 1.

Next, a probe for hybridization was prepared for confirming homology of a PHAsynthase gene of P91 strain. In the same manner as in Example 2, an oligonucleotide having the sequences of SEQ ID NOs 7 and 8 were synthesized. (Amersham-Pharmacia Biotech) PCR was conducted using the thus synthesized oligonucleotide as a primer and the chromosome DNA as a template. The obtained PCR amplified DNA fragments were used as a probe. Labeling of the probe using AlkphosDirect (Amersham-Pharmacia Biotech) was conducted to obtain the labeled probe referred to as "phaC1". In the same manner as above, an oligonucleotide having the sequences of SEQ ID NOs 9 and 10 were synthesized. (Amersham-Pharmacia Biotech) PCR was conducted using the thus synthesized oligonucleotide as a primer and the chromosome DNA as a template. Labeling of the obtained PCR amplified DNA fragments was conducted in the same manner as above to obtain the labeled probe referred to as "phaC2".

Using the thus obtained probes, homology of the PHA synthase gene was confirmed by a dot-blot method. The thus prepared chromosome DNA was alkalized and then blotted on a nylon film (Tropilon-45, produced by Tropix Co.) by 1 μg at respective portions using a dot-blot apparatus (BRL).

The film was dried at 80° C. for two hours, then put in a vinyl bag. 3 ml of the solution for hybridization prepared according to the recipe of AlkPhosDirect was added thereto, and hybridization was conducted at 55° C. for one hour. 15 ng of the labeled probe phaC1 or phaC2 per 3 ml of the above hybridization solution (5 ng/ml) was added to the nylon film, and hybridization was conducted at 55° C. for 12 hours. And then the nylon film was put out from the vinyl bag, and washed two times for 10 minutes at 55° C. with a first washing buffer according the recipe of AlkiPhosDirect. And then after it was washed two times for 5 minutes at room temperature with a second washing buffer according to the recipe of AlkPhosDirect, a detecting step was carried out using CDP-Star attached to AlkiPhosDirect according to the recipe.

Further, a detecting step was carried out under the same conditions as above except that hybridization and first washing were conducted at 60° C. or 65° C. The results were shown in Table 3 and 4.

TABLE 3

| Temperature (° C.) | 55 | 60 | 65 |
|---|---|---|---|
| Probe phaC1 Target DNA | | | |
| P91 Strain | A | A | B |
| ATCC29347 Strain | C | D | D |
| Probe phaC2 Target DNA | | | |
| P91 Strain | A | A | B |
| ATCC29347 Strain | C | D | D |

A: Strong Signal, B: Signal, C: Slight Signal, D: No Signal

TABLE 4

| Temperature (° C.) | 55 | 60 | 65 |
|---|---|---|---|
| Probe |  |  |  |
| phaC1 |  |  |  |
| Target DNA |  |  |  |
| P91 Strain | A | A | B |
| ATCC29347 Strain | C | D | D |
| KT2440 Strain | B | C | D |
| PAO1 Strain | D | D | D |

TABLE 4-continued

| Temperature (° C.) | 55 | 60 | 65 |
|---|---|---|---|
| Probe |  |  |  |
| phaC2 |  |  |  |
| Target DNA |  |  |  |
| P91 Strain | A | A | B |
| ATCC29347 Strain | C | D | D |
| KT2440 Strain | D | C | D |
| PAO1 Strain | D | D | D |

A: Strong Signal, B: Signal, C: Slight Signal, D: No Signal

What is claimed is:

1. An isolated polyhydroxyalkanoate synthase having the amino acid sequence of SEQ ID NO: 1.

2. An isolated polyhydroxyalkanoate synthase having an amino acid sequence, which is at least 95% homologous with the amino acid sequence of SEQ ID NO: 1.

3. A method for preparing the polyhydroxyalkanoate synthase according to claim 1 or 2, comprising the steps of:
  culturing the transformed microorganism harboring a recombinant vector containing a DNA sequence encoding the polyhydroxyalkanoate synthase in a medium;
  expressing said DNA; and
  isolating the polyhydroxyalkanoate synthase from the culture obtained.

4. A method according to claim 3, wherein the DNA has the sequence according to SEQ ID NO: 2.

* * * * *

UNITED STATES PATENT AND TRADEMARK OFFICE
CERTIFICATE OF CORRECTION

PATENT NO. : 6,812,013 B2
DATED : November 2, 2004
INVENTOR(S) : Tetsuya Yano et al.

It is certified that error appears in the above-identified patent and that said Letters Patent is hereby corrected as shown below:

Title page,
Item [56], References Cited, OTHER PUBLICATIONS,
"U. Pleper et al.," reference, "U. Pleper" should read -- U. Pieper --; and "Microbiol I." should read -- Microbiol. -- and "Poly(3–hydroxialkan ic acid" should read -- Poly(3–hydroxyalkanic acid --.
"H. Matsusaki et al.," reference, "Poly)3–" should read -- Poly(3– --; and "3–hydroxyalkanote)" should read -- (3–hydroxyalkanoate) --.
"D.M. Becker et al.;" reference, "M thods" should read -- Methods --.

Column 3,
Line 20, "in" should read -- is --.

Column 4,
Line 5, "overallperiphery," should read -- overall periphery --.

Column 5,
Line 42, "λgT10," should read -- λgt10, --.

Column 7,
Line 21, "Plabobacterium sp.," should read -- Flavobacterium sp., --;
Line 25, "Coryncbacterium sp., Artbrobacter sp.," should read -- Corynebacterium sp., Arthrobacter sp., --; and
Line 45, "trp." should read -- trp, --.

Signed and Sealed this

Nineteenth Day of April, 2005

JON W. DUDAS
*Director of the United States Patent and Trademark Office*